United States Patent
Hur et al.

(10) Patent No.: US 9,689,002 B2
(45) Date of Patent: Jun. 27, 2017

(54) METHODS FOR PREPARING TE(O) FROM TE(IV) USING METAL-REDUCING BACTERIA AND IRON ION

(71) Applicant: GWANGJU INSTITUTE OF SCIENCE AND TECHNOLOGY, Gwangju (KR)

(72) Inventors: Hor-Gil Hur, Gwangju (KR); Dong-Hun Kim, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 38 days.

(21) Appl. No.: 14/520,964

(22) Filed: Oct. 22, 2014

(65) Prior Publication Data

US 2015/0111274 A1    Apr. 23, 2015

(30) Foreign Application Priority Data

Oct. 22, 2013  (KR) ......................... 10-2013-0126207

(51) Int. Cl.
*C12P 3/00*        (2006.01)
*C01B 19/00*      (2006.01)

(52) U.S. Cl.
CPC ............... *C12P 3/00* (2013.01); *C01B 19/00* (2013.01)

(58) Field of Classification Search
None
See application file for complete search history.

(56) References Cited

FOREIGN PATENT DOCUMENTS

KR    1020100102851 A    9/2010

OTHER PUBLICATIONS

Kim ("Biological accumulation of tellurium nanorod structures via reduction of tellurite by Shewanella oneidensis MR-1" Bioresource Technology 125 (2012) 127-131.*
Shaun M. Baesman et al., Formation of Tellurium Nanocrystals during Anaerobic Growth of Bacteria That Use Te Oxyanions as Respiratory Electron Acceptors, Journal, Apr. 2007, p. 2135-2143, vol. 73, No. 7, American Society for Microbiology.
Thomas Girard Chasteen et al., Tellurite: history, oxidative stress, and molecular mechanisms of resistance, Article, 2009, pp. 820-832, FEMS Microbiol Rev 33, Blackwell Publishing Ltd.
E.A. Deliyanni et al., Removal of zinc ion from water by sorption onto iron-based nanoadsorbent, Journal, 2007, pp. 176-184, Journal of Hazardous Materials 141, Elsevier.
Jong-Min Oh, Geomicrobiological study of anaerobic microorganisms from KURT groundwater: Microbial diversity and reduction of Fe(III), Mn(III/IV), Cr(VI), Se(VI), Thesis, 2009, pp. 57-72, Department of Earth and Environmental Science Graduate School, Chonnam National University.
Ji-Noon Lee et al., Organic Acid-Dependent Iron Mineral Formation by a Newly Isolated Iron-Reducing Bacterium, *Shewanella* sp. HN-41, Journal, 2007, pp. 31-41, Taylor & Fancis Group, LLC, Geomicrobiology Journal.

(Continued)

*Primary Examiner* — Robert Yamasaki
*Assistant Examiner* — Charles Zoltan Constantine
(74) *Attorney, Agent, or Firm* — Hauptman Ham, LLP

(57) ABSTRACT

Disclosed is a method for preparing Te(O) in a low toxic form from toxic Te(IV) using metal-reducing bacteria and iron ions. According to the present invention, extracellular tellurium nanorods can be prepared through an environmentally friendly process and are able to provide tellurium utilizable in petroleum refining, electronic devices, batteries, and sensors.

10 Claims, 13 Drawing Sheets

(56) References Cited

OTHER PUBLICATIONS

Emmanuelle Liger et al., Surface catalysis of uranium(VI) reduction by iron(II), 1999, pp. 2939-2955, vol. 63, No. 19120, Elsevier science Ltd.

Shashwati Sen et al., Chlorine gas sensors using one-dimensional tellurium nanostructures, 2009, pp. 1567-1572, Elsevier B.V.

Y.C. Sharma et al., Nano-adsorbents for the removal of metallic pollutants from water and wastewater, Article, 2009, pp. 583-609, Taylor & Francis.

Lawrence L. Stookey, Ferrozine—A New Spectrophotometric Reagent for Iron, 1970, pp. 779-781, vol. 42, No. 7, Analytical Chemistry.

Zhiyong Tang et al., Self-Assembly of CdTe Nanocrystals into Free-Floating Sheets, Reports, 2006, pp. 274-278, vol. 314, Science AAAS.

Diane E. Taylor, Bacterial tellurite resistance, 1999, pp. 111-115, vol. 7, No. 3, Trends in Microbiology, Elsevier Science.

Raymond J. Turner et al., Microbial processing of tellurium as a tool in biotechnology, 2012, pp. 954-963, Elsevier.

Xiujuan Wang et al., Quinone-mediated reduction of selenite and tellurite by *Escherichia coli*, Article, 2011, pp. 3268-3271, vol. 102, Elsevier Ltd.

Davide Zannoni et al., The Bacterial Response to the Chalcogen Metalloids Se and Te, 2007, pp. 1-71, vol. 53, Advances in Microbial Physiology, Elsevier Ltd.

(Exception to Loss of Novelty) Dong-Hun Kim et al., Promoted Reduction of Tellurite and Formation of Extracellular Tellurium Nanorods by Concerted Reaction between Iron and Shewanella oneidensis MR-1, published in the Environmental Science & Technology on Jun. 26, 2013, pp. 8709-8715, vol. 47, ACS Publications.

(Exception to Loss of Novelty) Published at the 246th American chemical Society national Meeting & Exposition on Sep. 8, 2013.

* cited by examiner

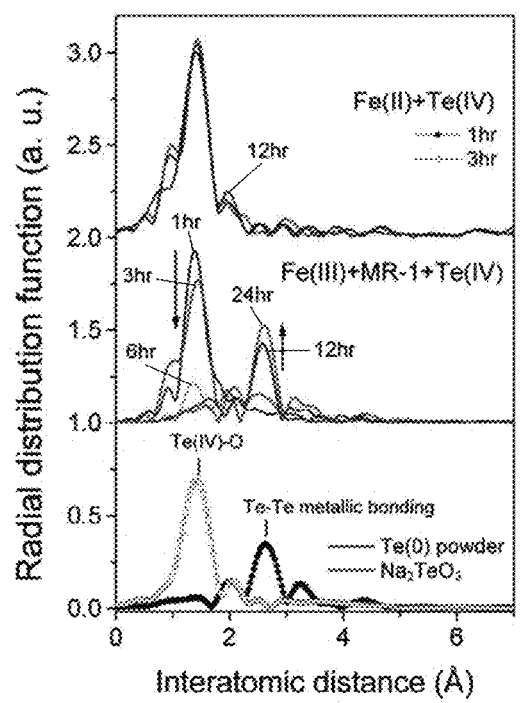

METHODS FOR PREPARING TE(O) FROM TE(IV) USING METAL-REDUCING BACTERIA AND IRON ION

CROSS REFERENCE TO RELATED APPLICATION

This application claims the benefit of Korean Patent Application No. 10-2013-0126207, filed on Oct. 22, 2013, entitled "METHODS FOR PREPARING TE(O) FROM TE(IV) USING METAL-REDUCING BACTERIA AND IRON ION", which is hereby incorporated by reference in its entirety into this application.

BACKGROUND

1. Technical Field

The present invention relates to a method for preparing Te(O) in a low toxic form from toxic Te(IV) using metal-reducing bacteria and iron ions.

2. Description of the Related Art

Tellurium (Te) and its compounds are widely used in petroleum refining, electronic and photoelectronic industries, optics, glass and sensors (Sen, S. et al., *Talanta* 2009, 77 (5), 1567-1572; Tang, Z. et al. *Science* 2006, 314 (5797), 274-8; Turner, R. J. et al. *Biotechnol. Adv.* 2012, 30 (5), 954-963; Wang, X. et al. *Bioresour. Technol.* 2011, 102 (3), 3268-71). However, recently expanded use of Te has led to environmental contamination (Chasteen, T. G. et al. *FEMS Microbiol. Rev.* 2009, 33 (4), 820-32). In the environment, water soluble tellurite oxyanions ($TeO_3^{2-}$, Te(IV)) are highly toxic to both eukaryotic and prokaryotic cells at concentrations as low as 1 µg/ml (Chasteen, T. G. et al. *FEMS Microbiol. Rev.* 2009, 33 (4), 820-32; Zannoni, D. et al. *Adv. Microb. Physiol.* 2007, 53, 1-71).

The redox chemistry of Te is crucial in governing mobility and toxicity. The elemental state of Te(O) is insoluble in water and has low bioavailability and toxicity. Therefore, the reduction of Te(IV) to insoluble and less toxic Te(O) is an effective strategy for relieving the high toxicity of Te(IV) in the environment. Several recent studies have shown that Te can be removed from aqueous solution via the reduction of Te(IV) to insoluble and low toxic forms (Turner, R. J. et al. *Biotechnol. Adv.* 2012, 30 (5), 954-963; Wang, X. et al. *Bioresour. Technol.* 2011, 102 (3), 3268-71; Taylor, D. E. *Trends Microbiol.* 1999, 7 (3), 111-5; Baesman, S. M. et al. *Appl. Environ. Microbiol.* 2007, 73(7), 2135-43).

The biogeochemical cycles of major and trace elements in the environment are driven by redox processes, which also affect the chemical species, bioavailability, toxicity, and mobility of the elements. Especially, the most abundant iron ion on the Earth's surface plays a particularly important role in environmental biogeochemistry. In fact, the soluble Fe(II) produced by reduction of iron oxide and Fe-bearing minerals by various biogeochemical reactions can act as a powerful reducing agent in a variety of abiotic redox processes (Liger, E. et al. *Geochim. Cosmochim. Acta* 1999, 63 (19-20), 2939-2955).

The disclosures of all cited articles and patent publications referred to in this specification are incorporated herein by reference in their entirety to enable a person having ordinary knowledge in the art to more clearly understand the technical field and context of the present invention.

BRIEF SUMMARY

In order to solve problems relating to environmental contamination and toxicity of Te(IV), the present inventors have made an effort to develop an environmentally friendly method. As a result, the inventors of the present invention have found that toxic Te(IV) is capable of being reduced to Te(O) in a low toxic form having a nanorod shape by culturing iron-reducing bacteria together with Fe(III) or Fe(II) in the presence of Te(IV). Based on such finding, the inventors completed the present invention.

Therefore, it is an object of the present invention to provide a method for preparing Te(O) in a low toxic form from toxic Te(IV).

It is another object of the present invention to provide a method for converting toxic Te(IV) to Te(O) into a low toxic form.

It is a further object of the present invention to provide Te(O) prepared by the above method.

Other objects and advantages of the present invention will be described more clearly by the following detailed description of the present invention, the attached claims and the drawings.

In accordance with one aspect of the present invention, a method for preparing Te(O) in a low toxic form from toxic Te(IV) includes culturing Fe(III)-reducing bacteria in a medium by adding an electron donor, Te(IV) and Fe(III) to the medium or by adding an electron donor, Te(IV) and Fe(II) to the medium.

In accordance with another aspect of the present invention, a method for preparing Te(O) in a low toxic form from toxic Te(IV) includes culturing Fe(III)-reducing bacteria in a medium to form Fe(II) by adding an electron donor and Fe(III) to the medium; and culturing the medium to form Te(O) by adding Te(IV) to the medium.

In accordance with a further aspect of the present invention, a method for converting toxic Te(IV) to Te(O) in a low toxic form includes: culturing Fe(III)-reducing bacteria in a medium by adding an electron donor, Te(IV) and Fe(III) to the medium or by adding an electron donor, Te(IV) and Fe(II) to the medium.

In accordance with yet another aspect of the present invention, a method for converting toxic Te(IV) to Te(O) in a low toxic form includes: culturing Fe(III)-reducing bacteria in a medium by adding an electron donor and Fe(III) to form Fe(II) to the medium; and culturing the medium by adding Te(IV) to form Te(O) to the medium.

The present inventors have made an effort to develop an environmentally friendly method to solve problems related to environmental contamination and toxicity due to Te(IV). As a result, the inventors of the present invention have found that toxic Te(IV) is capable of being reduced to Te(O) in a low toxic form having a nanorod shape by culturing iron-reducing bacteria together with Fe(III) or Fe(II) in the presence of Te(IV).

As shown in FIG. 11, culturing of *Shewanella oneidensis* MR-1 in the presence of Te(IV) leads to the formation of Te(O) nanorods, wherein intracellular Te(O) nanorods are formed, and the reaction rate is slow. However, when the above microorganism is cultured together with Te(IV) in the presence of iron ions (Fe(III) or Fe(II)) as in the present invention, extracellular Te(O) nanorods are formed, and the reaction rate is fast. In contrast, reaction of Fe(II) and Te(IV) in the absence of *Shewanella oneidensis* MR-1 strains only leads to the formation of tellurite ($Te(IV)O_x$) precipitates.

In the present invention, the Fe(III)-reducing bacteria refer to strains having a capacity of reducing Fe(III) to Fe(II). Additionally, the Fe(III)-reducing bacteria have a capacity of reducing tellurite (Te(IV)) to elemental tellurium (Te(O)).

According to one embodiment of the invention, the Fe(III)-reducing bacteria utilizable in the present invention include genus *Shewanella* bacteria. Genus *Shewanella* microorganisms are marine bacteria and are capable of conducting iron respiration under anaerobic conditions. In a specific embodiment, genus *Shewanella* bacteria are either *Shewanella oneidensis* MR-1 (ATCC 700550) or genus *Shewanella* sp. HN-41 (KCTC 10837BP).

The medium utilized in order to maintain growth and activity of bacteria in reduction by means of the Fe(III)-reducing bacteria may be any medium known in the art, for example, HEPES-buffered standard medium may be utilized (Lee J-H, et al. *Geomicrobiol J* 2007, 24:31-41).

According to one embodiment of the invention, the cultivation of Fe(III)-reducing bacteria is carried out under anaerobic conditions.

The electron donor provides electrons for the Fe(III)-reducing bacteria to reduce Fe(III) and tellurite (Te(IV)). The electron donor utilizable in the present invention is not particularly limited. For example, electron donors in salt form may be utilized.

According to one embodiment of the invention, the electron donor is lactate.

According to the present invention, Te(O) may be prepared by culturing Fe(III)-reducing bacteria in the presence of an electron donor, Te(IV) and Fe(III), wherein Fe(III) is reduced to Fe(II) by microorganisms, the reduced Fe(II) reduces Te(IV) to tellurite (Te(IV)$O_x$), and the tellurite(Te (IV)$O_x$) is converted into Te(O) nanostructures by the microorganisms.

According to one embodiment of the invention, the Te(O) nanostructures prepared by culturing Fe(III)-reducing bacteria with the electron donor, Te(IV) and Fe(III) have a length of 120 nm to 360 nm and a width of 20 nm to 30 nm. In one particular example, the nanostructures have an average length of 220 nm to 260 nm.

Optionally, Te(IV) may be added to a medium after Fe(III) is reduced to Fe(II) by the Fe(III)-reducing bacteria. Namely, in the present invention, Te(IV) may be added to a medium as an initial material, or may be added after Fe(III) is reduced to Fe(II) by the microorganism. As can be seen from the following examples, Te(O) prepared by adding Te(IV) in consecutive order has a tendency to show a shorter length and thinner width as compared with Te(O) nanostructures prepared by culturing Fe(III)-reducing bacteria in the presence of Te(IV) and Fe(III). Therefore, the length and width of the Te(O) nanostructures may be controlled by adjusting the timing of adding Te(IV).

According to one embodiment of the invention, the nanostructures prepared by reducing Fe(III) to Fe(II) by the Fe(III)-reducing bacteria, followed by adding Te(IV), have a length of 60 nm to 150 nm and a width of 3 nm to 10 nm. In one particular example, the nanostructures have an average length of 75 nm to 110 nm.

According to one embodiment of the invention, Te(O) nanostructures are formed outside(extracellular) the Fe(III)-reducing bacteria.

According to one embodiment of the invention, the Te(O) nanostructures are formed in the shape of nanorods.

In accordance with yet further aspect of the present invention, the present invention provides Te(O) prepared in the shape of nanorods by the method according to the present invention.

Since Te(O) having a nanorod shape according to the present invention is prepared by the method described above, any common features between nanorod-shaped Te(O) and the method may be omitted in order to avoid excessive complexity.

The technical features and advantages of the present invention are summarized as follows:

(i) The present invention suggests a novel method for preparing Te(O) in a low toxic form from toxic Te(IV) using Fe(III)-reducing bacteria;

(ii) According to the present invention, extracellular tellurium nanorods can be prepared through an environmentally friendly process; and (iii) The present invention is able to provide tellurium utilizable in petroleum refining, electronic devices, batteries, and sensors.

BRIEF DESCRIPTION OF THE DRAWINGS

The above and other aspects, features, and advantages of the present invention will become apparent from the detailed description of the following embodiments in conjunction with the accompanying drawings, in which:

FIG. 1(*b*) shows Fe(II) (b) in aqueous phase under various incubation conditions. *S. oneidensis* MR-1 was incubated with Fe(III) and Te(IV) under anaerobic conditions;

FIG. 4(*b*) shows corresponding radial distribution function of $k_2$-weighted Te K-edge extended X-ray absorption fine structure (EXAFS) for both incubation time in biological reduction (Fe(III)+Te(IV)+*S. oneidensis* MR-1) and reaction time in abiological reduction (Fe(II)+Te(IV)+no bacterial inoculation). In each plot, metallic tellurium powder (Te(O), filled circle ●) and tellurite ($Na_2TeO_3$, open circle ○) were compared;

DETAILED DESCRIPTION

Figure 1A:
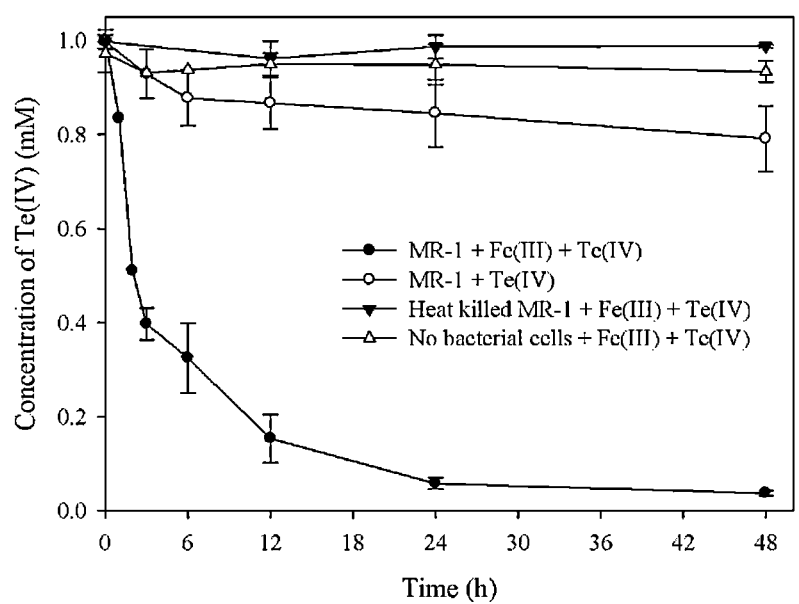
FIG. 1(*a*) shows kinetics of Te(IV) in aqueous phase under various incubation conditions. *S. oneidensis* MR-1 was incubated with Fe(III) and Te(IV) under anaerobic conditions.

Hereinafter, embodiments of the invention will be described in detail with reference to the accompanying drawings. It should be understood that the present invention is not limited to the following embodiments and may be embodied in different ways, and that the embodiments are given to provide complete disclosure of the invention and to provide thorough understanding of the invention to those skilled in the art. The scope of the invention is limited only by the accompanying claims and equivalents thereof. Like components will be denoted by like reference numerals throughout the specification.

EXAMPLES

Experimental Materials and Methods

Chemicals, Bacterial Strains and Culture Conditions

All chemicals and reagents were purchased from Sigma-Aldrich (St. Louis, Mo.) and Fisher Scientific (Pittsburgh, Pa.). The facultative anaerobic bacterium *S. oneidensis* MR-1 was grown aerobically on Luria-Bertani (LB) broth at 30° C. with shaking at 200 rpm for 12 hours. Cells were centrifuged (9000 g for 10 min), washed with sterile HEPES buffer (10 mM, pH 7.0), and resuspended in HEPES buffer. Cells were subsequently inoculated into serum bottles to achieve an optical density (OD) of 0.1 at a wavelength of 600 nm of the total volume of sterilized HEPES-buffered basal medium, which contained 10 mM sodium lactate (0.22 μm filter sterilized) as an electron donor and other chemicals were added according to reaction conditions. To evaluate the effect of diverse reducing agents on Te(IV) reduction, 10 mM each of Fe(III)-citrate, akaganeite, manganese oxide, sodium thiosulfate, sodium fumarate, and sodium nitrate were added to HEPES-buffered basal medium which contains lactate, *S. oneidensis* MR-1, and 1 mM Te(IV) under anaerobic conditions. Direct reduction of Te(IV) by *S. oneidensis* MR-1 was tested with 10 mM lactate and 1 mM Te(IV) as an electron donor and acceptor, respectively. All incubations were performed in triplicate and carried out in the absence of light without agitation at 30° C. under anaerobic conditions.

Analytic Methods

The culture medium was periodically sampled during incubation to determine the concentration of Fe(II) and Te(IV) in solution phase. For each sample, 1 mL of culture medium was collected at the selected time and then immediately passed through a 0.22 μm membrane filter (MFS-25, Adantec MFS, Inc., Dublin, Calif.). The concentration of Fe(II) was monitored spectrophotometrically at 562 nm using ferrozine assay (Stookey, L. L. *Anal. Chem.* 1970, 42 (7), 779-781). To measure Te(IV) concentration, the aqueous phase was diluted with 2% (v/v) $HNO_3$ and analyzed by inductively coupled plasma-mass spectroscopy (ICP-MS, 7500 ce, Agilent Technology, Palo Alto, Calif.). All measurements were conducted in triplicate. The mineralogical properties of the nanostructures were analyzed using powder X-ray diffraction (XRD, D/MAX Ultima III, Rigaku, Tokyo, Japan) emitting with monochromatic high-intensity Cu Kα radiation (λ=1.54056 Å).

Electron Microscopic Analyses

The formation and accumulation of tellurium nanostructures in the bacterial culture medium were periodically determined by SEM and TEM analyses during reaction period. Samples were collected at a selected time and centrifuged at 9000 g for 5 minutes. The pellets were washed three times and resuspended in deionized water, and dropped onto a silica wafer for SEM imaging (XL30-FEG, Philips, Eindhoven, Netherlands). For TEM imaging, washed cells were placed onto carbon-coated 200-mesh copper grids. The images of whole mounts were obtained at 200 kV using a JEOL JEM-2100 high resolution TEM (JEOL, Tokyo, Japan).

Te K-Edge X-ray Absorption Spectroscopy (XAS)

Te K-edge X-ray absorption spectra, X-ray absorption near edge structure (XANES) and extended X-ray absorption fine structure (EXAFS), were collected on the BL10C beamline at the Pohang light source (PLS-II) with a ring current of 100 mA at 3.0 GeV. The monochromatic X-ray beam could be obtained from high intensity X-ray photons of a multipole wiggler source using liquid-nitrogen cooled Si (III) double crystal monochromator (Bruker ASC). The X-ray absorption spectroscopic data were recorded for the uniformly dispersed powder samples with a proper thickness on the polyimide film, in transmission mode with $N_2$ gas-filled ionization chambers. All samples were maintained in an Ar atmosphere before XAFS measurement in order to remove any airborne contamination leading to sample oxidation. Higher order harmonic contaminations were eliminated by detuning to reduce the incident X-ray intensity by ~20%. Energy calibration was simultaneously carried out for each measurement with reference Te metal powder placed in front of the third ion chamber. The data reductions of the experimental spectra to normalized XANES and Fourier-transformed radial distribution function (RDF) were performed through the standard XAFS procedure.

Experimental Results

Effects of Diverse Reducing Agents on Te(IV) Reduction in the Culture of *S. oneidensis* MR-1

The effects of diverse reducing agents, Fe(III)-citrate, akaganeite, manganese oxide, sodium thiosulfate, sodium fumarate, and sodium nitrate, as an electron shuttle on the reduction of Te(IV) in the anaerobic culture of *S. oneidensis* MR-1 was examined.

As a result, as shown in Table 1, the reduction rate of Te(IV) by *S. oneidensis* MR-1 was significantly increased when akaganeite, Fe(III)-citrate, and manganese oxide were added to the bacterial culture as compared with when *S. oneidensis* MR-1 alone was added. The initial concentration of Te(IV) at 1 mM was reduced up to 99%, 94%, and 76% within 24 hours in the bacterial culture of *S. oneidensis* MR-1 containing akaganeite, Fe(III)-citrate, and manganese oxide, respectively. The higher reduction of Te(IV) by *S. oneidensis* MR-1 with akaganeite than that strain MR-1 with Fe(III)-citrate could be attributed to adsorption of Te(IV) ions onto the insoluble akaganeite structure as suggested in previous reports (Deliyanni, E. A. et al. *J. Hazard. Mater.* 2007, 141 (1), 176-84; Sharma, Y. C. et al., *Environ. Technol.* 2009, 30 (6), 583-609). In contrast, Te(IV) was reduced by 16%, 22%, and 10% using a culture of *S. oneidensis* MR-1 with thiosulfate, fumarate, and nitrate, respectively, in 24-hour incubation, indicating addition of Fe(III) to the culture of *S. oneidensis* MR-1, which stimulated the reduction of Te(IV).

TABLE 1

| Reactions | Concentration of Te(IV) remained in the aqueous phase at 24 h incubation (mM) |
| --- | --- |
| Control (culture medium alone) | 0.97 ± 0.03 |
| *S. oneidensis* MR-1 alone | 0.85 ± 0.03 |
| *S. oneidensis* MR-1 + Fe(III)-citrate | 0.06 ± 0.01 |
| *S. oneidensis* MR-1 + Akaganeite | 0.02 ± 0.01 |
| *S. oneidensis* MR-1 + Manganese oxide | 0.49 ± 0.13 |
| *S. oneidensis* MR-1 + Thiosulfate | 0.84 ± 0.06 |
| *S. oneidensis* MR-1 + Fumarate | 0.78 ± 0.05 |
| *S. oneidensis* MR-1 + Nitrate | 0.96 ± 0.04 |

Effects of Fe(III) and Fe(II) on Te(IV) Reduction in the Culture of *S. oneidensis* MR-1

A further experiment was performed to better understand the effects of iron on the Te(IV) reduction by *S. oneidensis* MR-1 under anaerobic conditions. FIG. 1a shows that kinetics of Te(IV) reduction varies under different incubation conditions. *S. oneidensis* MR-1 in the presence of Fe(III) at 10 mM dramatically increased Te(IV) reduction by up to 61.7% in 3 hour incubations, as compared with the reaction conditions without either Fe(III) or *S. oneidensis* MR-1, which did not show Te(IV) reduction. Although the MR-1 culture in the absence of Fe(III) showed barely 10% Te(IV) reduction in 3 h incubation, no further significant reduction of Te(IV) occurred as incubation time passed. The lesser reduction of 1 mM Te(IV) is possibly due to physiological toxicity of Te(IV) to the strain.

Figure 1B:
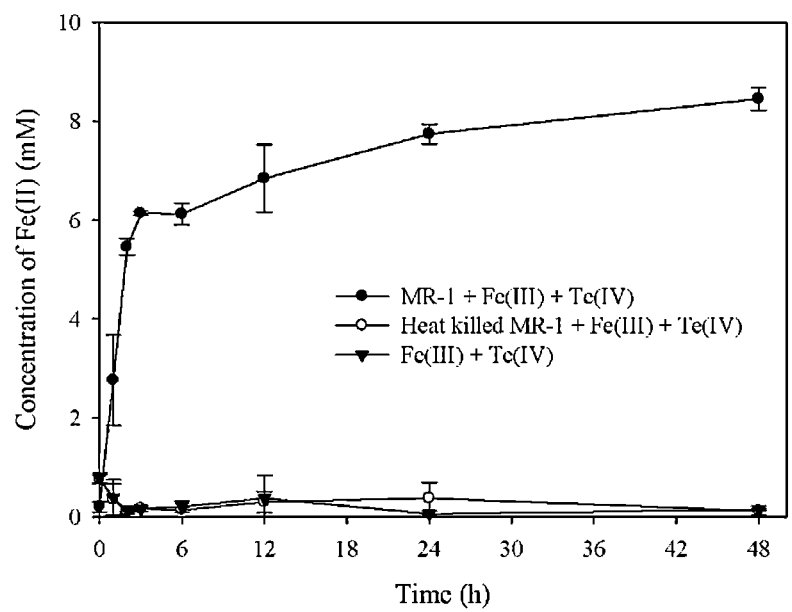

In addition, the heat-killed *S. oneidensis* MR-1 with Fe(III) or Fe(III) alone did not show Te(IV) reduction. While monitoring the kinetics of Te(IV) reduction by *S. oneidensis* MR-1 in the presence of Fe(III) under anaerobic conditions, the oxidation state of iron (Fe(III) and Fe(II)) was also tracked (FIG. 1b). The amount of Fe(II) in the culture medium of *S. oneidensis* MR-1 in the presence of Fe(III) and Te(IV) at each of 10 mM and 1 mM, respectively, was increased with increasing incubation period. *S. oneidensis* MR-1 rapidly produced Fe(II) at approximately 6 mM in 3 h incubation, and then maintained Fe(II) at 8.5 mM to the end of incubation. In contrast, controls containing Fe(III) with the heat-killed bacterial cells and Fe(III) alone did not produce Fe(II) and did not reduce Te(IV) to Te(O). These results suggested that reducing power for Te(IV) reduction could be supported chemically from Fe(II) produced by *S. oneidensis* MR-1.

Figure 2:
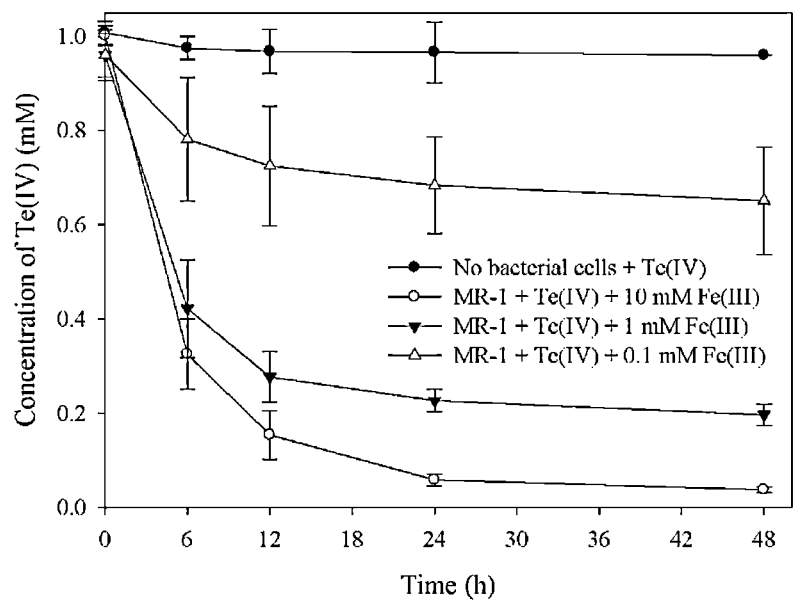
FIG. 2 shows kinetics of Te(IV) in aqueous phase. *S. oneidensis* MR-1 was incubated with Fe(III) at various concentrations and 0.1 mM of Te(IV) under anaerobic conditions.

Fe(III) concentration also has an effect on Te(IV) reduction in the presence of *S. oneidensis* MR-1 strain. Higher concentration of Fe(III) showed a greater rate of Te(IV) reduction than evident at low concentration of Fe(III) (FIG. 2). In the presence of *S. oneidensis* MR-1 strain, 10 mM of Fe(III) showed more than 94% reduction of Te(IV) while 1 mM and 0.1 mM of Fe(III) showed 76% and 29% of Te(IV) reduction, respectively, at 24-hour incubation. There could be another possibility of direct chemical reduction of Te(IV) by a chemical reducing reagent such as Fe(III) ion.

Figure 3:
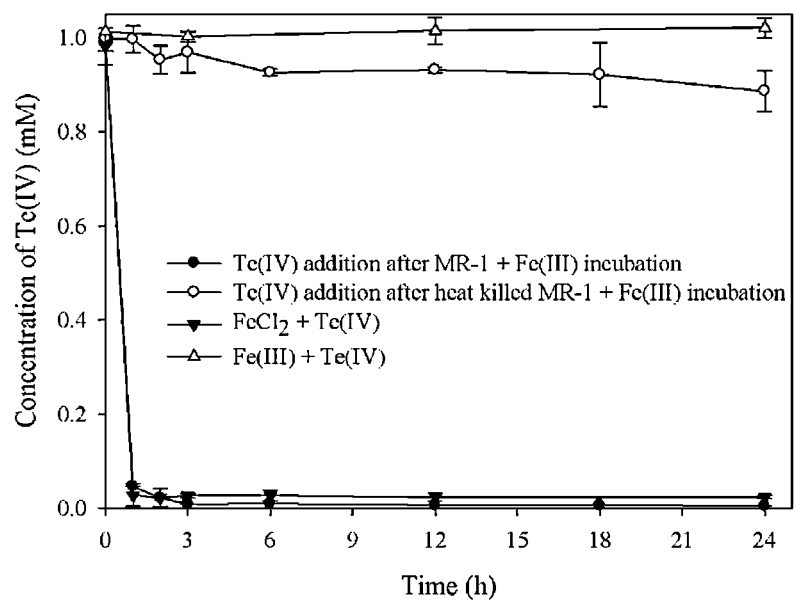
FIG. 3 shows kinetics of Te(IV) and Fe(II) in aqueous phase under various incubation conditions. Active or heat killed *S. oneidensis* MR-1 was pre-incubated with Fe(III) for 24 hours and abiological Fe(II) and Fe(III) were prepared as $FeCl_2$ and Fe(III)-citrate.

To test for chemical reduction of Te(IV) by Fe(II) in the absence of *S. oneidensis* MR-1, $FeCl_2$ at 10 mM in the final concentration was added to the solution containing Te(IV). Initial Te(IV) in media containing abiological Fe(II) rapidly decreased more than 97% in 1 hour reaction (FIG. 3). In addition, similar results were also observed in the bacterial culture where biological Fe(II) was pre-formed by *S. oneidensis* MR-1 with Fe(III) for 24-hour incubation. The bacterial culture with pre-formed biological Fe(II) reduced Te(IV) more than 95% of initial Te(IV) within 1-hour reaction. In contrast, the Te(IV) reduction reaction was not observed in the absence of Fe(II).

Figure 4A:
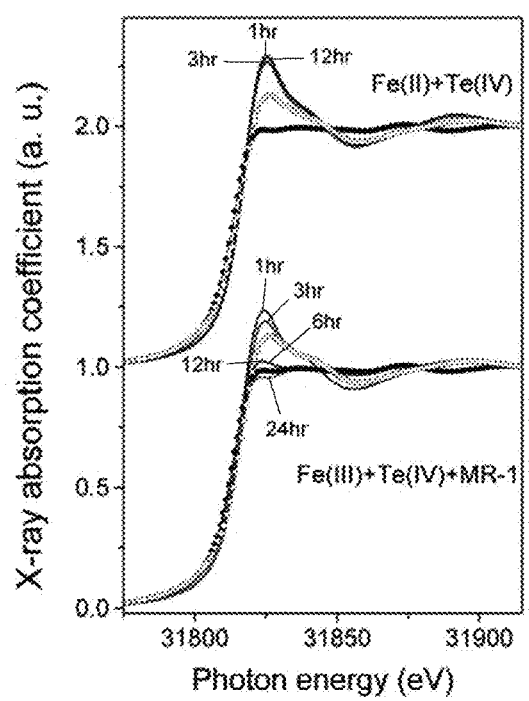
FIG. 4(*a*) shows normalized Te K-edge X-ray absorption near edge structure (XANES) for both incubation time in biological reduction (Fe(III)+Te(IV)+*S. oneidensis* MR-1) and reaction time in abiological reduction (Fe(II)+Te(IV)+ no bacterial inoculation). In each plot, metallic tellurium powder (Te(O), filled circle ●) and tellurite ($Na_2TeO_3$, open circle ○) were compared.

It should be noted that the X-ray absorption spectroscopic study revealed the chemical reduction of Te(IV) by Fe(II) in the absence of *S. oneidensis* MR-1 was not able to proceed to total reduction to metallic Te(O) state, but was likely to precipitate from the solution in the form of tellurite (Te(IV)$O_x$). This is supported by the normalized Te K-edge X-ray absorption near edge structure (XANES) and the corresponding radical distribution function of Fourier-transformed $k_2$-weighted Te K-edge extended X-ray absorption fine structure (EXAFS) for incubation time in both biological reduction (Fe(III)+Te(IV)+*S. oneidensis* MR-1) and chemical reduction (Fe(II)+Te(IV)) (FIG. 4). Concretively, as shown in FIG. 4a, the Te K-edge XANES spectra for abiological Fe(II)-mediated reduction in the absence of *S. oneidensis* MR-1 present a constant tellurite-like XANES peak feature even given a reaction time of 12 hours, while biological reduction of Te(IV) in the presence of *S. oneidensis* MR-1 surely leads to more distinct metallic tellurium-like XANES feature with increasing incubation time.

In the radial distribution function of EXAFS spectra in FIG. 4b, the biological reduction of Te(IV) in the presence of *S. oneidensis* MR-1 presents an abrupt decrease of Fourier-transformed (FT) peak for chemical bonding Te(IV)-O at ~1.45 Å with respect to incubation time, and a distinct development of Fourier-transformed (FT) peak at ~2.6 Å corresponding to metallic Te—Te interaction. In contrast, the abiological reduction of Te(IV) to by Fe(II) shows a constant Te(IV)-O bonding and no FT peak of metallic bonding Te—Te, regardless of chemical reaction time.

This suggests that the toxic Te(IV) ion cannot be effectively reduced by the chemical reducing Fe(II) ion itself, although the Fe(II) is able to promote precipitation of solid tellurite (Te(IV)$O_x$) complex from the Te(IV) solution. Therefore, the existence of *S. oneidensis* MR-1 is certainly necessary to reduce the tellurite (Te(IV)) to metallic tellurium (Te(O)).

The biological reduction of Te(IV) in the presence of *S. oneidensis* MR-1 started to shows only the FT peak of Te(O)-O bonding in 1 hour incubation, underwent to evolve the FT peak of the metallic bonding Te—Te from 3 hour incubation, and terminated the formation of metallic FT peak in 12 hours (FIG. 4). These results demonstrate that the Te(IV) in a biological medium is not immediately reduced at the moment of initial reaction but rather reduction effectively begins after 3 h incubation.

The spectroscopic results suggest that *S. oneidensis* MR-1 in biological reduction leads to initial reduction of Fe(III) to Fe(II) in the solution followed by the precipitation of tellurite (Te(IV)$O_x$), which is likely further reduced into less harmful metallic Te(O) through biological respiration by *S. oneidensis* MR-1.

Figure 5:
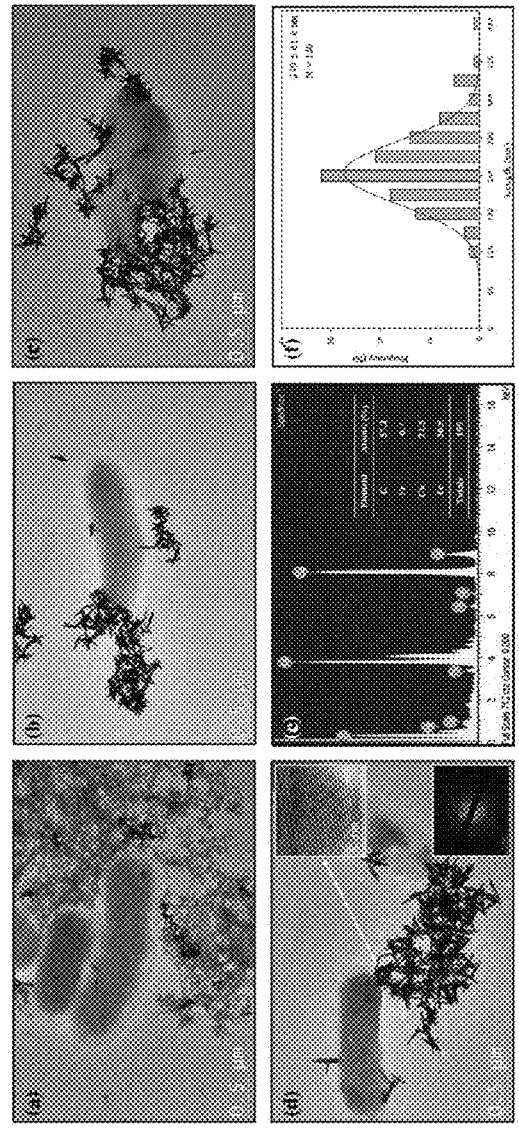
FIG. 5 shows TEM images (a) to (d) for extracellular Te(O) nanorods formed by concurrent incubation of Fe(III) with Te(IV) in the presence of *S. oneidensis* MR-1 with SAED pattern (d inserted), EDS spectra (e), and length distribution (f) at 24 hour incubation. The TEM images of (a) to (d) were taken at 1, 3, 12 and 24 hour incubation, respectively.

Morphological Analyses of Tellurium Nanostructures Formed under Various Incubation Conditions During the incubation of *S. oneidensis* MR-1 in the presence of both Fe(III) and Te(IV), the color of the incubation medium changed to black, followed by precipitation of the black particles. In contrast, color change and precipitation were not observed in the control experiments lacking either Fe(III) or active *S. oneidensis* MR-1 cells. In addition, direct bacterial Te(IV) reduction by *S. oneidensis* MR-1 in the absence of either Fe(III) or Fe(II) also displayed blackening, leading to mostly intracellular and/or surface accumulation of Te(O) nanorods. However, TEM images showed that *S. oneidensis* MR-1 in the presence of both Fe(III) and Te(IV) together abundantly accumulated extracellular Te(O) nanostructures (FIG. 5). With the incubation time, Fe and Te were initially aggregated around the bacterial cells at 1 hour incubation (FIG. 5a), followed by formation of the needle-shaped Te(O) nanorods at 3 hour incubation (FIG. 5b). The Te(O) nanorod structures accumulated continuously on the bacterial cell surface during incubation (FIG. 5c, d). The selected area electron diffraction (SAED) patterns revealed that the Te(O) nanorods were well-crystallized structures (FIG. 5d). Energy-dispersive X-ray spectroscopy (EDS) analysis of the Te(O) nanorods illustrates a composition of 97% Te and 3% Fe (FIG. 5e). The length and width of the Te(O) nanorods determined by measuring the 120 nanorods were in the range of 240 and 25 nm, respectively (FIG. 5f).

Figure 6:
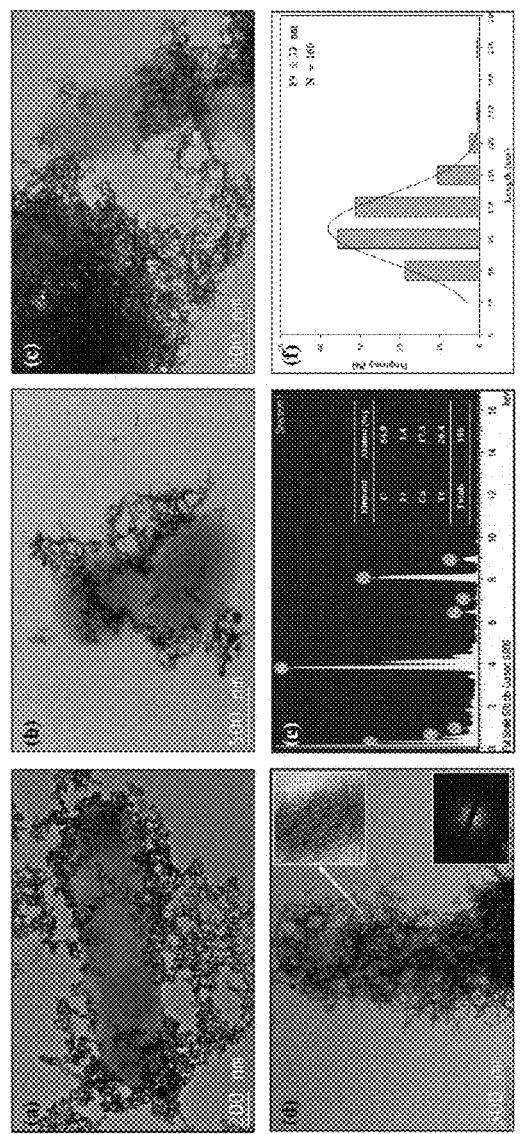
FIG. 6 shows TEM images (a) to (d) for extracellular Te(O) nanorods formed by preformed Fe(II) with Te(IV) in the presence of *S. oneidensis* MR-1 for 24 hours with SAED pattern (d inserted), EDS spectra (e) and length distribution (f) at 24 hour incubation. The TEM images of (a) to (d) were taken at 1, 3, 12 and 24 hours after incubation was initiated, respectively.
Figure 7:
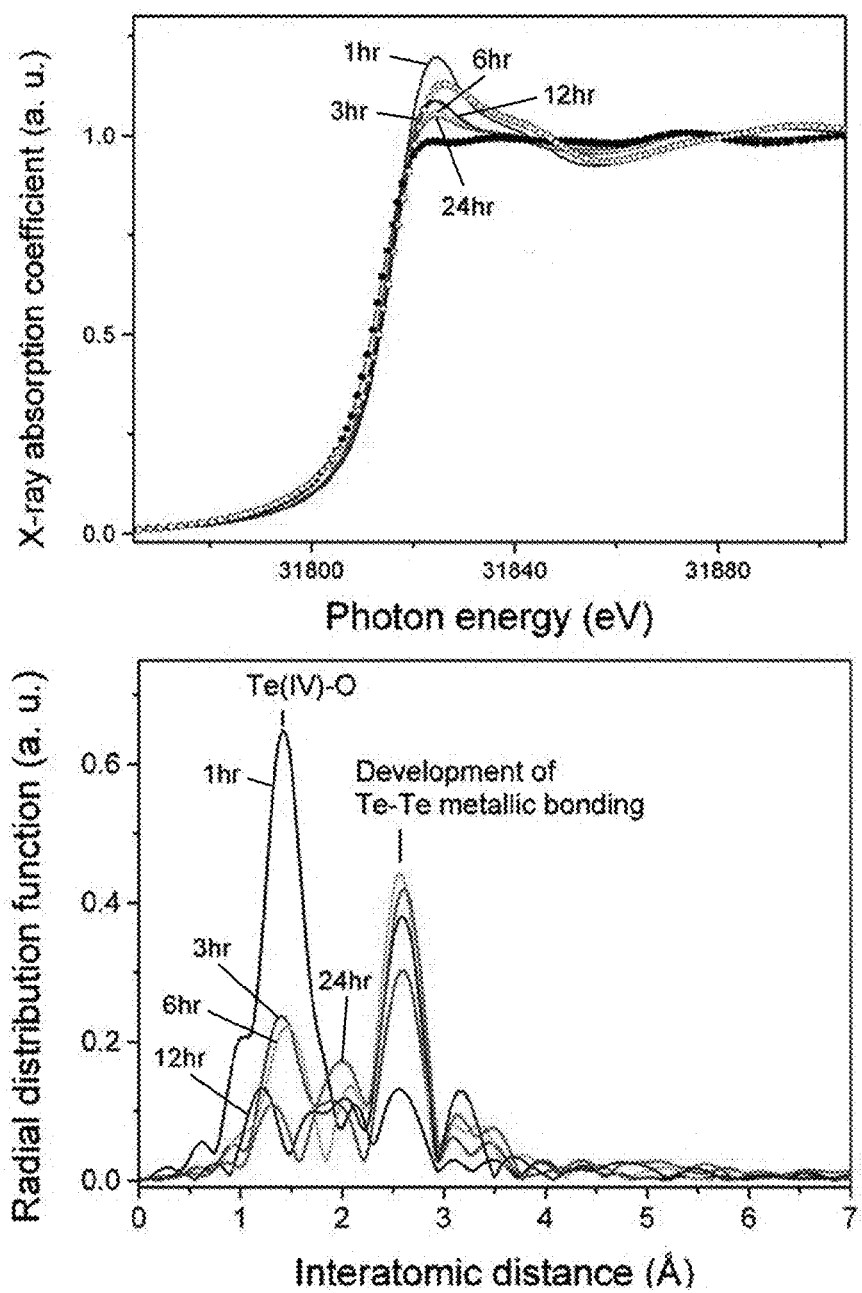
FIG. 7 shows (a) normalized Te K-edge XANES for Te-related structure formed by Te(IV) and pre-formed Fe(II) (upper) and (b) corresponding radial distribution function of $k_2$-weighted Te K-edge EXAFS (bottom) in the incubation of *S. oneidensis* MR-1. In each plot, metallic tellurium powder (Te(O), filled circle ●) and $Na_2TeO_3$ tellurite (open circle ○) were compared.

*S. oneidensis* MR-1 was preincubated with Fe(III) for 24 hours to produce Fe(II), and then Te(IV) was added to the bacterial culture. Interestingly, the morphology of the Te(O) nanorods was shorter and thinner than that of Te(O) nanorods formed by the bacterial culture in the presence of Fe(III) and Te(IV) together (FIGS. 5 and 6). TEM images illustrated numerous accumulated extracellular Te(O) nanostructures (FIG. 6). Initial Fe and Te aggregates at 1 hour incubation (FIG. 6a) were transformed into needle-shaped Te(O) nanorods at 3 hours (FIG. 6b), followed by continuous accumulation of Te(O) nanorods on the bacterial cell surfaces during the period of incubation (FIG. 6c, d). The high-resolution TEM (HR-TEM) image and SAED patterns revealed that the Te(O) nanorods formed by the preformed Fe(II) with Te(IV) in the presence of *S. oneidensis* MR-1 had crystallized structures (FIG. 6d). EDS analysis of the Te(O) nanorods illustrates a composition of 97% Te and 3% Fe (FIG. 6e). The length and width of the Te(O) nanorods determined by measuring the 160 nanorods were in the range of 89 nm and 7.5 nm, respectively (FIG. 6f). The XAFS study for Te(IV) reduction after preincubation of Fe(III) in the presence of *S. oneidensis* MR-1 shows different XANES and EXAFS peak features (FIG. 7). Unlike the aforementioned reaction in the concurrent existence of Fe(III), Te(IV), and *S. oneidensis* MR-1 in culture medium, the XANES and FT peak features for Te(O) nanorods formed by the preformed Fe(II) with Te(IV) in the presence of *S. oneidensis* MR-1 demonstrated the metallic peak characteristics in the initial 1 hour biological reduction. This suggests that the Te(IV) ion in the solution of preformed Fe(II) in the presence of *S. oneidensis* MR-1 is immediately reduced in the initial reaction followed by the formation of metallic tellurium Te(O) particles.

Figure 8:
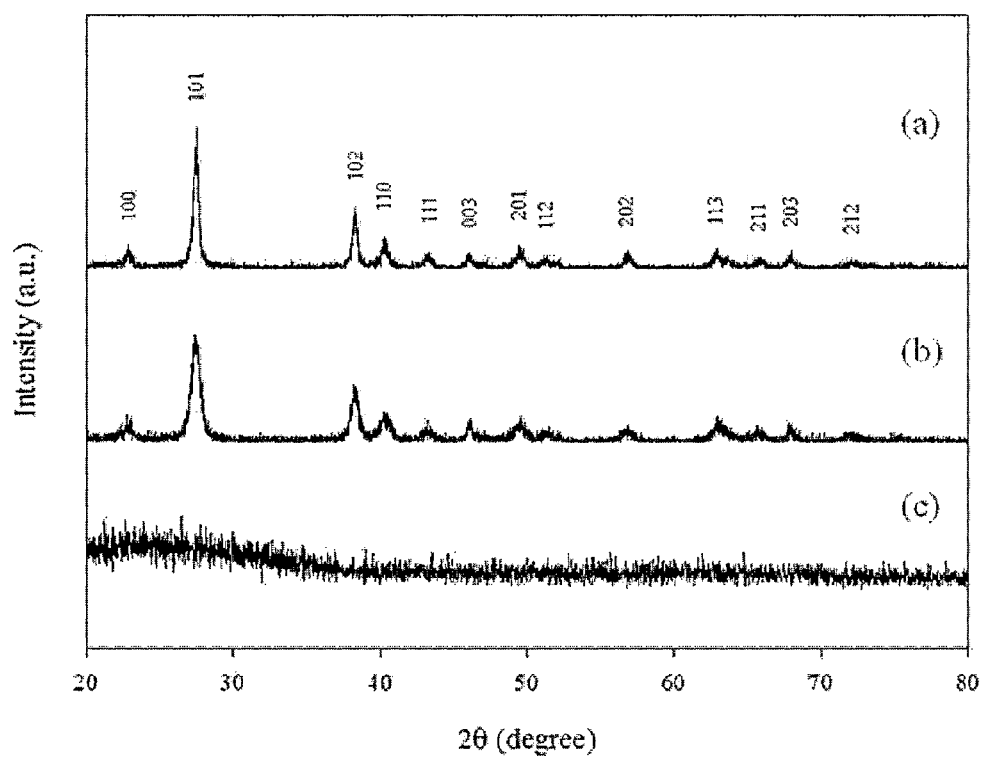
FIG. 8 shows XRD patterns of Te nanostructures formed by Fe(III) and Te(IV) in the presence of *S. oneidensis* MR-1 (a), pre-formed Fe(II) and Te(IV) in the presence of *S. oneidensis* MR-1 (b), and abiological Fe(II) and Te(IV) in the absence of strains (c), after 24-hour incubation.
Figure 9:
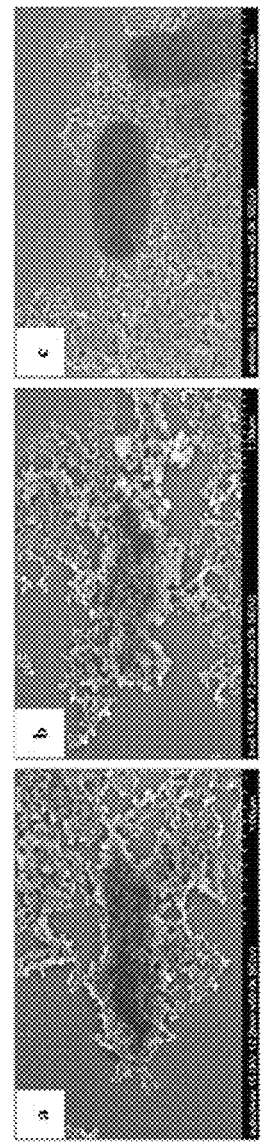
FIG. 9 shows SEM images of Te nanostructures produced by pre-formed Fe(II) and Te(IV) in the presence of heat killed bacteria cells subjected to heat for 20 minutes (a) and autoclaving for 20 minutes (b) or in the presence of metabolically inactivated bacteria cells by the addition of kanamycin (50 μg/ml) (c) at 24 hours reaction.

The phases of products formed by concurrent incubation of Fe(III) and Te(IV) in the presence of *S. oneidensis* MR-1 (FIG. 8a), preformed Fe(II) with Te(IV) in the presence of *S. oneidensis* MR-1 (FIG. 8b), and abiological Fe(II) with Te(IV) in the absence of *S. oneidensis* MR-1 (FIG. 8c) were identified by X-ray diffraction. All of the diffraction peaks were indexed on a hexagonal structure of tellurium (space group P3121 (no. 152), powder diffraction file No. 36-1452). However, abiological Fe(II)-mediated Te nanoparticles formed in the absence of *S. oneidensis* MR-1 did not exhibit crystal characteristics (FIG. 8c), which was consistent with the X-ray absorption spectroscopic analyses (FIG. 4). These results indicate that Fe(III) or Fe(II)-mediated Te nanorods produced in the presence of *S. oneidensis* MR-1 were a single phase of well-crystallized elemental Te(O) with a hexagonal structure. In addition, preformed Fe(II) with Te(IV) in the presence of heat killed bacterial cells or in the presence of metabolically inactivated bacterial cells treated with adding kanamycin (50 μg/mL) did not produce the rod-shaped Te(O) structures while forming only aggregates of tellurite (Te(IV)$O_x$) after 24 hour reaction (FIG. 9).

Figure 10:
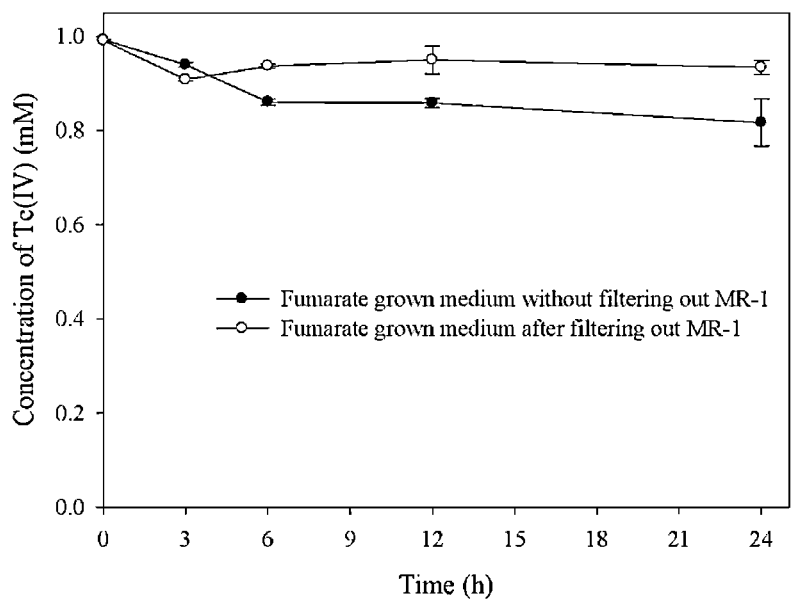
FIG. 10 shows kinetics of Te(IV) in an aqueous phase pre-incubated with fumarate in the presence of *S. oneidensis* MR-1. Te(IV) was added to a medium in the presence or absence of *S. oneidensis* MR-1.
Figure 11:
FIG. 11 shows procedures to form Te(O) nanorods in accordance with the present invention.

Experiments were also conducted to test the possibility that water-soluble chemical reductants or redox-active proteins were released by *S. oneidensis* MR-1 during metabolism of lactate that might cause extracellular Te(IV) reduction. These cell-free experiments, filtrates of culture medium after growth of *S. oneidensis* MR-1 with lactate and 10 mM of fumarate, were used to test 1 mM Te(IV) reduction under anaerobic conditions. There was no Te(IV) reduction observed (FIG. 10), suggesting Te(IV) reduction was started by Fe(II) production from Fe(III) in the presence of *S. oneidensis* MR-1. Taken together, the results clearly indicate that bacterial *S. oneidensis* MR-1 plays important roles in the shape formation and crystallization of Te(O) nanorods from precipitates as evidenced by the XANES and EXAFS spectral analyses above.

Although some exemplary embodiments have been described herein, it should be understood by those skilled in the art that these embodiments are given by way of illustration only, and that various modifications, variations and alterations can be made without departing from the spirit and scope of the invention. The scope of the present invention should be defined by the appended claims and equivalents thereof.

What is claimed is:

1. A method for preparing extracellular Te(O) nanostructure in a low toxic form from toxic Te(IV), comprising:
    culturing Fe(III)-reducing bacteria in a medium comprising an electron donor, Te(IV) and Fe(III), or an electron donor, Te(IV) and Fe(II),
    wherein Fe (III) when present is reduced to Fe(II) by the Fe(III)-reducing bacteria,
    Fe(II) reduces Te(IV) to tellurite (Te(IV)$O_x$),
    the Fe(III)-reducing bacteria convert the tellurite into the TeO nanostructure outside of the bacterial cells, and
    Te and Fe compose the Te(O) nanostructure.
2. A method for preparing extracellular Te(O) nanostructure in a low toxic form from toxic Te(IV), comprising:

pre-incubating Fe(III)-reducing bacteria in a medium comprising an electron donor and Fe(III) to form Fe(II)

adding Te(IV) to the medium comprising the formed Fe(II); and culturing the Fe(III)-reducing bacteria in the medium to form extracellular Te(O) nanostructure, wherein Fe(III) is reduced to Fe(II) by Fe(III)-reducing bacteria, Fe(II) reduces Te(IV) to tellurite (Te(IV)O$_x$), the Fe(III)-reducing bacteria convert the tellurite into the TeO nanostructure outside of the bacterial cells, Te and Fe compose the Te(O) nanostructure, and the Te(O) nanostructure has a shorter length and a thinner width as compared with a Te(O) nanostructure prepared by culturing Fe(III)-reducing bacteria in a medium comprising Te(IV) and Fe(III) without pre-incubating.

3. The method for preparing extracellular Te(O) nanostructure in a low toxic form according to claim 2, wherein the Fe(III)-reducing bacteria are genus *Shewanella* bacteria.

4. The method for preparing extracellular Te(O) nanostructure in a low toxic form according to claim 3, wherein the genus *Shewanella* bacteria are *Shewanella oneidensis* MR-1 (ATCC 700550).

5. The method for preparing extracellular Te(O) nanostructure in a low toxic form according to claim 2, wherein the pre-incubating is performed under anaerobic conditions.

6. The method for preparing extracellular Te(O) nanostructure in a low toxic form according to claim 2, wherein the Te(O) nanostructure is formed in the shape of nanorods.

7. The method for preparing extracellular Te(O) nanostructure in a low toxic form according to claim 6, wherein the nanorods have a length of 120 nm-360 nm.

8. The method for preparing extracellular Te(O) nanostructure in a low toxic form according to claim 6, wherein the nanorods have a length of 60 nm-150 nm.

9. A method for converting toxic Te(IV) to Te(O) in a low toxic extracellular form, comprising:

culturing Fe(III)-reducing bacteria in a medium comprising an electron donor, Te(IV) and Fe(III), or an electron donor, Te(IV) and Fe(II), wherein Fe (III) when present is reduced to Fe(II) by the Fe(III)-reducing bacteria, Fe(II) reduces Te(IV) to tellurite, the Fe(III)-reducing bacteria convert the tellurite into the TeO nanostructure outside of the bacterial cells, and Te and Fe compose the Te(O) nanostructure.

10. The method for converting toxic Te(IV) to Te(O) in a low toxic extracellular form according to claim 9, wherein the Fe(III) or Fe(II) is in a concentration of 0.1 mM to 10 mM.

* * * * *